(12) United States Patent
Johnson et al.

(10) Patent No.: US 10,716,475 B2
(45) Date of Patent: Jul. 21, 2020

(54) LOCALIZED MONITORING

(71) Applicant: ZOLL Medical Corporation, Chelmsford, MA (US)

(72) Inventors: Guy R. Johnson, Gloucester, MA (US); Gary A. Freeman, Newton Center, MA (US)

(73) Assignee: Zoll Medical Corporation, Chelmsford, MA (US)

( * ) Notice: Subject to any disclaimer, the term of this patent is extended or adjusted under 35 U.S.C. 154(b) by 164 days.

(21) Appl. No.: 14/036,501

(22) Filed: Sep. 25, 2013

(65) Prior Publication Data

US 2015/0087920 A1    Mar. 26, 2015

(51) Int. Cl.
*A61B 5/00*   (2006.01)
*A61B 5/0402*   (2006.01)
*A61N 1/39*   (2006.01)
*A61B 5/0205*   (2006.01)
*A61B 5/145*   (2006.01)
*A61B 5/021*   (2006.01)
*A61B 5/08*   (2006.01)

(52) U.S. Cl.
CPC .......... *A61B 5/0024* (2013.01); *A61B 5/0006* (2013.01); *A61B 5/0028* (2013.01); *A61B 5/0402* (2013.01); *A61B 5/7221* (2013.01); *A61N 1/39* (2013.01); *A61N 1/3925* (2013.01); *A61B 5/021* (2013.01); *A61B 5/02055* (2013.01); *A61B 5/0816* (2013.01); *A61B 5/14532* (2013.01); *A61B 5/14542* (2013.01)

(58) Field of Classification Search
CPC ... A61B 5/0028; A61B 5/0024; A61B 5/7221; H04B 13/005; A61N 1/39; A61H 2201/501; G06F 19/3418
See application file for complete search history.

(56) References Cited

U.S. PATENT DOCUMENTS

| | | | |
|---|---|---|---|
| 7,949,404 B2 * | 5/2011 | Hill | 607/60 |
| 8,105,249 B2 | 1/2012 | Freeman | |
| 8,204,589 B2 | 6/2012 | Freeman | |
| 8,321,011 B2 | 11/2012 | Parascandola et al. | |
| 8,457,560 B2 | 6/2013 | Rajagopal et al. | |
| 8,478,401 B2 | 7/2013 | Freeman | |
| 8,488,655 B2 | 7/2013 | Batra et al. | |

(Continued)

FOREIGN PATENT DOCUMENTS

WO    WO 2011/0008008    9/2011

OTHER PUBLICATIONS

Alim, M. Abdul, and Behcet Sarikaya. "EAP-Sens: a security architecture for wireless sensor networks." Proceedings of the 4th Annual International Conference on Wireless Internet. ICST (Institute for Computer Sciences, Social-Informatics and Telecommunications Engineering), 2008.*

(Continued)

*Primary Examiner* — Niketa I Patel
*Assistant Examiner* — Nathan A Baldwin
(74) *Attorney, Agent, or Firm* — Finch & Maloney PLLC

(57) ABSTRACT

This document relates to receiving and processing signals during cardio-pulmonary resuscitation (CPR) treatment. This document further relates to establishing a localized, patient-specific network for communication of information from one or more sensors to a computing device.

28 Claims, 6 Drawing Sheets

(56) References Cited

U.S. PATENT DOCUMENTS

| | | | |
|---|---|---|---|
| 8,665,896 B2 | 3/2014 | Patel | |
| 2004/0133242 A1* | 7/2004 | Chapman | A61B 5/0002 607/5 |
| 2004/0268119 A1* | 12/2004 | Smetters | H04L 9/00 713/155 |
| 2007/0027388 A1* | 2/2007 | Chou | 600/393 |
| 2007/0135866 A1* | 6/2007 | Baker et al. | 607/60 |
| 2008/0103370 A1* | 5/2008 | Dicks | G06F 19/3418 600/300 |
| 2008/0194925 A1 | 8/2008 | Alsafadi et al. | |
| 2009/0023391 A1* | 1/2009 | Falck | 455/41.2 |
| 2009/0069642 A1 | 3/2009 | Gao et al. | |
| 2009/0231125 A1* | 9/2009 | Baldus | A61B 5/0006 340/539.12 |
| 2010/0114254 A1* | 5/2010 | Kornet | 607/62 |
| 2011/0004073 A1 | 1/2011 | Corroy et al. | |
| 2011/0085505 A1 | 4/2011 | Kang et al. | |
| 2011/0182223 A1 | 7/2011 | Patel et al. | |
| 2011/0221590 A1 | 9/2011 | Baker et al. | |
| 2012/0092155 A1 | 4/2012 | Abedi | |
| 2012/0191476 A1 | 7/2012 | Reid et al. | |

OTHER PUBLICATIONS

Grigorik, Ilya. "High Performance Browser Networking." High Performance Browser Networking. O'Reilly Media, Inc., Mar. 16, 2013. Web. May 13, 2016. <http://chimera.labs.oreilly.com/books/1230000000545/ch02.html>.*

International Search Report and Written Opinion, PCT/US2014/056320, dated Dec. 31, 2014, 13 pages.

* cited by examiner

LOCALIZED MONITORING

TECHNICAL FIELD

This document relates to receiving and processing signals during cardio-pulmonary resuscitation (CPR) treatment. This document further relates to establishing a localized, patient-specific network for communication of information from one or more sensors to a computing device.

BACKGROUND

Sudden cardiac arrest (colloquially "heart attack") is a frequent cause of death. One treatment for cardiac arrest is quick and competent chest compressions to keep blood flowing through a patient's heart. Along with chest compressions, a rescuer may ventilate the patient by either exhaling into the patient's mouth or nose or utilizing a device that pushes air into the patient's lungs. Rescuers, in particular untrained rescuers, may benefit from feedback about performance of the CPR. Additionally, doctors or other healthcare workers such as emergency medical technicians (EMTs) may benefit from information about the patient's medical status during a rescue attempt. As such, it can be beneficial to gather information related to the patient status and/or performance of CPR from sensors.

SUMMARY

This document describes a system and method in which physiological monitors (e.g., sensors) associated with a patient use local communication for high speed low power communications. The monitors form a mesh network and communicate with a central computing device such as a defibrillator to gather information about the patient and/or the rescue attempt. In order to protect patient privacy and ensure the correct patient-specific wireless network is joined, joining the mesh network is restricted to authorized devices. In some examples, access to the wireless network can be provided only after successful completion of an authentication process in which one or more signals are transmitted via human body communication (HBC) where the patient's body is used as a transmission medium. Using the patient's body as a transmission medium ensures that various sensors joining the network are associated with the same patient.

In one aspect, a system includes a sensor configured to be placed in contact with the skin of a patient, an ECG lead configured to be placed in contact with the skin of the patient, and a computing device. The computing device is configured to establish a localized, patient-specific wireless network, perform an authentication process by sending multiple signals between the sensor and the computing device with at least one of the signals being transmitted between the sensor and the ECG lead using the patient's body as the conductive medium, and subsequent to the authentication process, enable the sensor to send and receive signals via the wireless network.

In another aspect, a medical system for providing electromagnetic stimulation of a patient includes an electronic interface configured to receive data from one or more sensors, an ECG lead configured to be placed in contact with the skin of the patient, and a computing device. The computing device is configured to establish a localized, patient-specific wireless network, perform an authentication process by sending one or more signals to the sensor and receiving one or more signals from the sensor, with at least one of the signals being transmitted between the sensor and the ECG lead using the patient's body as the conductive medium, and subsequent to the authentication process, enable the sensor to send and receive signals via the wireless network.

Embodiments can include one or more of the following.

The computing device can be further configured to initiate the authentication process based on a request to join the wireless network received from the sensor.

The configurations to perform the authentication process can include configurations to perform a handshaking routine during which at least one of the signals is transmitted using the patient's body as the conductive medium.

The wireless network can be a body area network.

The wireless network can be a mesh network.

In some additional aspects, a sensor device include a wireless transceiver configured to communicate with a computing device via a localized, patient-specific wireless network, a contact configured to be placed in contact with the skin of a patient, and a device configured to perform an authentication process by sending one or more signals to a computing device and receiving one or more signals from the computing device, with at least one of the signals being transmitted between the contact of the sensor and an ECG lead using the patient's body as the conductive medium. The device is further configured to join the patient-specific wireless network subsequent to the authentication process.

Embodiments can include one or more of the following.

The sensor can be further configured to initiate the authentication process by sending to the computing device a request to join the wireless network.

The configurations to perform the authentication process can include configurations to perform a handshaking routine during which at least one of the signals is transmitted using the patient's body as the conductive medium.

The wireless network can be a body area network.

The wireless network can be a mesh network.

The sensor can be configured to monitor at least one of blood pressure, temperature, respiration rate, blood oxygen level, end tidal carbon dioxide level, pulmonary function, and blood glucose level.

In some additional aspects, a method for providing a patient-specific wireless network includes establishing, by a computing device associated with a defibrillator, a wireless network, performing an authentication process that includes sending multiple signals between a sensor and the computing device with at least one of the signals being transmitted using the patient's body as the conductive medium, and subsequent to the authentication process, enabling the sensor to send and receive signals via the wireless network.

Embodiments can include one or more of the following.

The method can also include, prior to performing the authentication process, receiving, at the computing device from the sensor, a request to join the wireless network.

Performing the authentication process can include performing a handshaking routine during which at least one of the signals is transmitted using the patient's body as the conductive medium.

Performing the authentication process can include confirming that the sensor is in contact with the patient.

Sending the multiple signals with at least one of the signals being transmitted using the patient's body as the conductive medium can include sending at least one signal from the sensor, through the patient's body, and to an ECG lead.

The wireless network can be a body area network.

The wireless network can be a mesh network.

The wireless network can be a localized, patient-specific network.

The sensors can include one or more sensors configured to monitor at least one of blood pressure, temperature, respiration rate, blood oxygen level, end tidal carbon dioxide level, pulmonary function, and blood glucose level.

The method can also include securing one or more ECG leads to the body of the patient and securing the sensor to the body of the patient.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1:
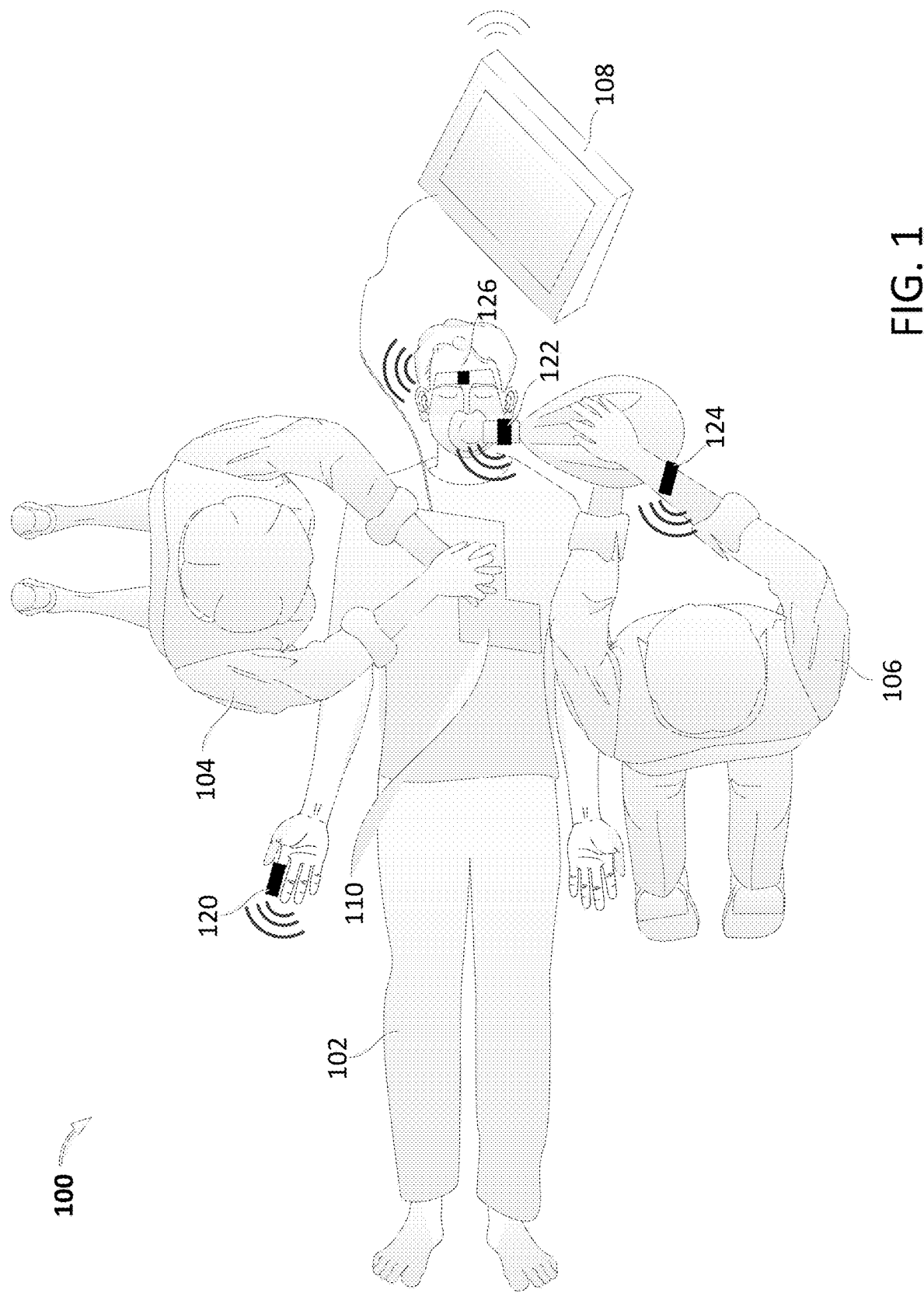
FIG. 1 illustrates caregivers using a system for responding to an emergency medical condition.

Referring to FIG. 1, at a rescue scene 100, a caregiver 104 performs cardiopulmonary resuscitation (CPR) on a victim or patient 102 (the terms are used interchangeably here to indicate a person who is the subject of intended or actual CPR and related treatment, or other medical treatment), such as an individual who has apparently undergone sudden cardiac arrest. The caregiver 104 may be, for instance, a civilian responder with limited or no training in lifesaving techniques; a first responder, such as an emergency medical technician (EMT), police officer, or firefighter; or a medical professional, such as a physician or nurse. The caregiver 104 may be acting alone or may be acting with assistance from one or more other caregivers, such as a partner EMT 106.

In this illustration, the caregivers 104 and 106 can deploy a defibrillator (such as an automated external defibrillator (AED) 108, a professional defibrillator, or another type of defibrillating apparatus) and multiple sensors 120, 122, 124, 126 for monitoring the patient and/or the rescuer. The sensors 120, 122, 124, 126 communicate wirelessly with the defibrillator 108 (or other computing device) over a patient-specific, localized network.

Exemplary sensors can include sensors to monitor heart rate and/or to generate electrocardiographs ("EGG's"). Heart rate and ECG sensors can be included in pads 110 of the defibrillator. Additional sensors gather other information about the patient's status and communicate wirelessly with the defibrillator 108. Such sensors may monitor, detect, treat and/or derive or calculate blood pressure, temperature, respiration rate, blood oxygen level, end-tidal carbon dioxide level, pulmonary function, blood glucose level, and/or weight. Since the sensors (e.g., sensors 120, 122, 124, 126) communicate wirelessly with the defibrillator 108, the number of wires surrounding the patient can be reduced. Reducing the number of wires can be advantageous, for example, when transporting or moving the patient. Additionally, it can be quicker and/or easier to deploy multiple sensors when the caregiver does not have to untangle or route wiring to the defibrillator 108.

In order to provide wireless communication between the multiple sensors and the central computing device (e.g., defibrillator 108 or another computing device such as a portable computer), a local area network is established. The network is designed to be patient-specific, such that only devices/sensors involved in the monitoring and treatment of the patient are included in the wireless network. The network can take the form of an ad hoc, self-configuring, self-healing network such as a mesh network. Wireless mesh networks are multi-hop systems in which devices assist each other in transmitting packets through the network, especially in adverse conditions. Such ad hoc networks may be implemented with minimal preparation, and they can provide a reliable, flexible system that can be extended to many devices (e.g., the network can support multiple sensors associated with the patient and the caregivers).

In a wireless mesh network, multiple nodes cooperate to relay a message to its destination. The mesh topology enhances the overall reliability of the network, which is particularly important when operating in harsh industrial environments. Like the Internet and other peer-to-peer router-based networks, a mesh network offers multiple redundant communications paths throughout the network. If one link fails for any reason (including the introduction of strong RF interference), the network automatically routes messages through alternate paths. In a mesh network, the distance between nodes can be shortened, which dramatically increases the link quality. A network may be a self-configuring and self-healing network. A network may not require a system administrator to tell it how to get a message to its destination. A mesh network can be self-organizing and does not require manual configuration. Because of this, adding new sensors or relocating existing sensors is as simple as turning the sensor on. The network can discover the new node and automatically incorporate it into the existing system/network.

Figure 2:
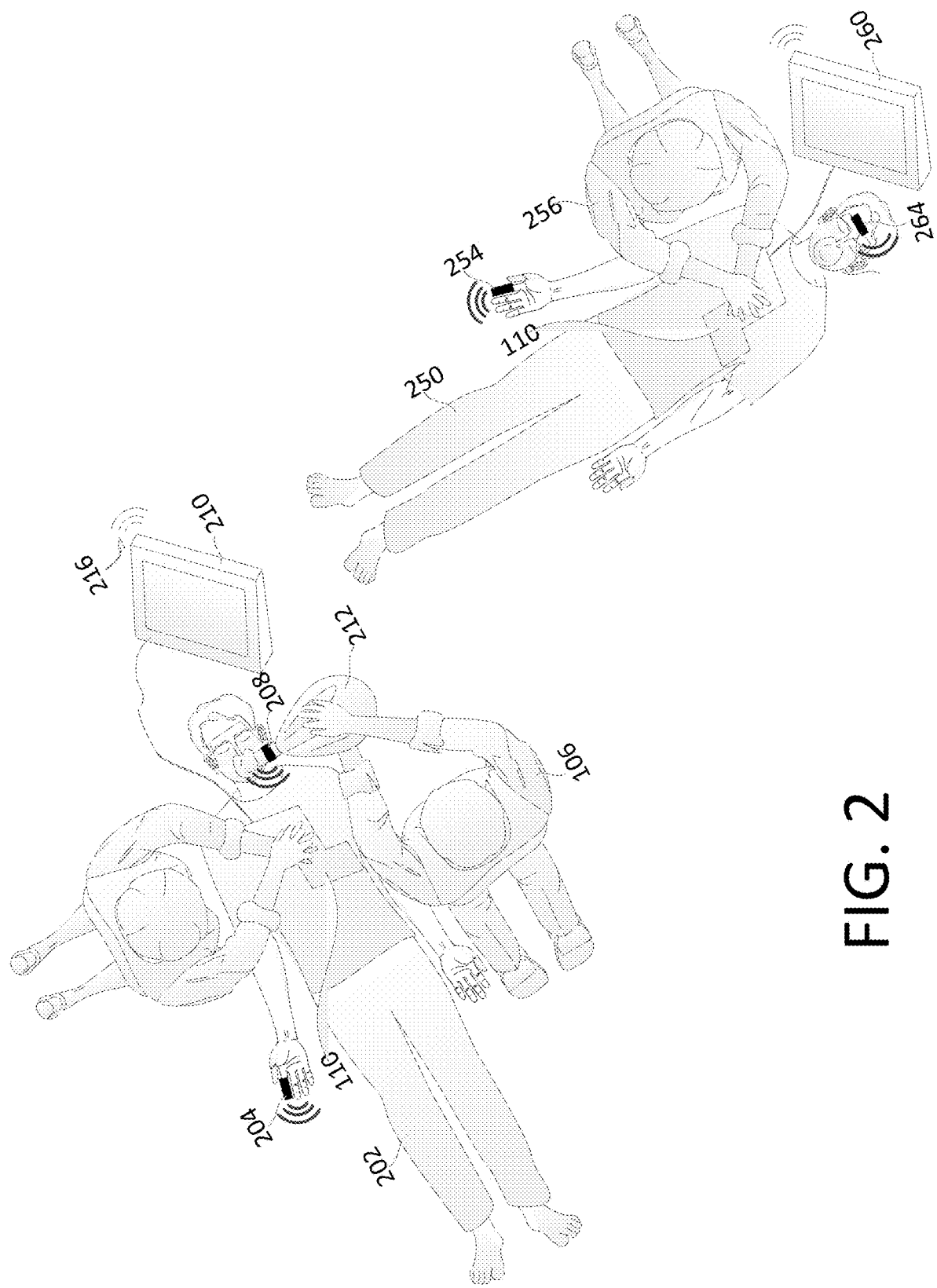
FIG. 2 illustrates multiple caregivers responding to a mass casualty event.

In systems such as those described herein where various sensors communicate wirelessly with a central computing device, such as the defibrillator, it is important to ensure that the sensors are paired with the correct central computing device. For example, as shown in FIG. 2, at the scene of a mass casualty or mass rescue event, there can be multiple different patients 202, 250. It is essential that the sensors for a particular patient are correctly paired with the computing device or defibrillator associated with that patient. For example, sensors, 204 and 208, which are used to monitor the status of patient 202 should be wirelessly connected with the central computing element in defibrillator 210 while the sensors 254 and 264 used to monitor the status of patient 250 should be wirelessly connected to the central computing element in defibrillator 260. If, for example, the sensors 204 and 208 associated with patient 202 were instead mistakenly wirelessly connected to defibrillator 260, the information used to analyze the status of victim 250 could be compromised. In an extreme case, if patient 202 regained blood circulation and breathing and the sensors were mistakenly connected to the defibrillator 260, defibrillator 260 could erroneously instruct the rescuer 256 to discontinue administration of CPR on victim 250. In another example, if ECG information were erroneously transmitted to an incorrectly matched defibrillator, the defibrillator could erroneously shock a victim whose heart rhythm was non-shockable. In order to prevent such detrimental situations, it is important to ensure that the sensors are paired with the correct central computing device.

Additionally, it is important that the sensors are correctly paired with an appropriate central computing device to ensure that confidential patient data is not disseminated to an unintentional recipient. Correct pairing of the sensors and the computing device ensures that patient-specific data is only received by those authorized to view and use such information.

Correct pairing of a sensor with the patient-specific, localized network occurs when the sensor is connected to the wireless network. More particularly, the pairing occurs during an initialization process includes authentication of the sensor to join the network. This authentication process is designed to ensure that a sensor is, in fact, associated with the patient prior to enabling the sensor to join the wireless network for the patient.

Figure 3A:
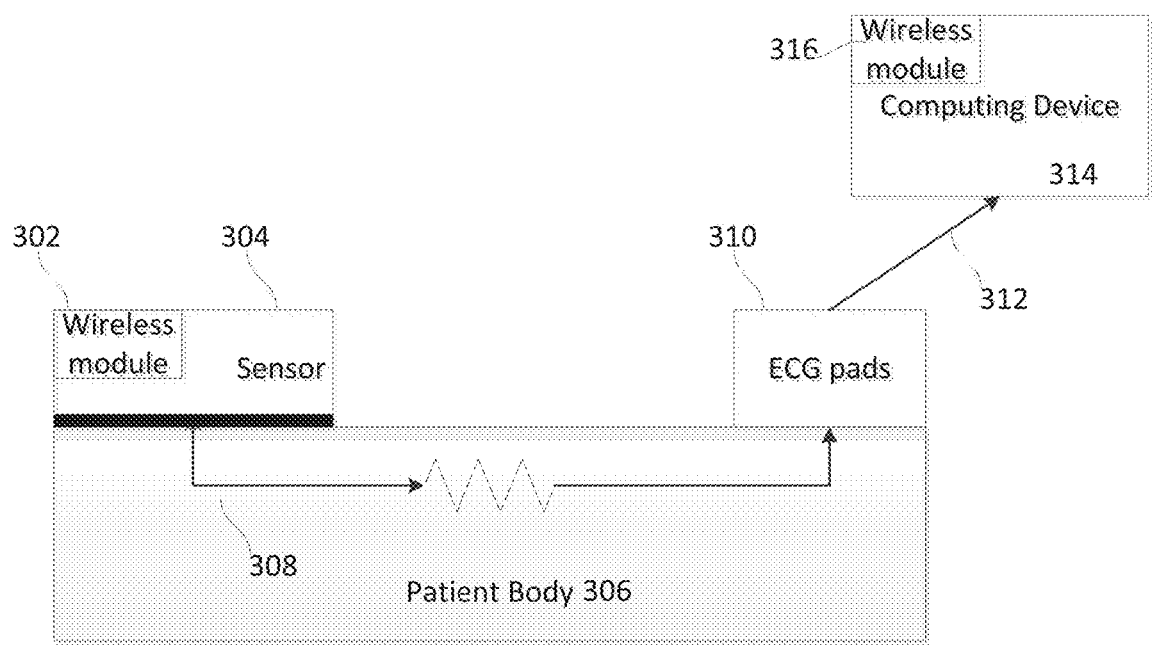
FIGS. 3A and 3B show communication paths between a sensor and computing device.
Figure 3B:
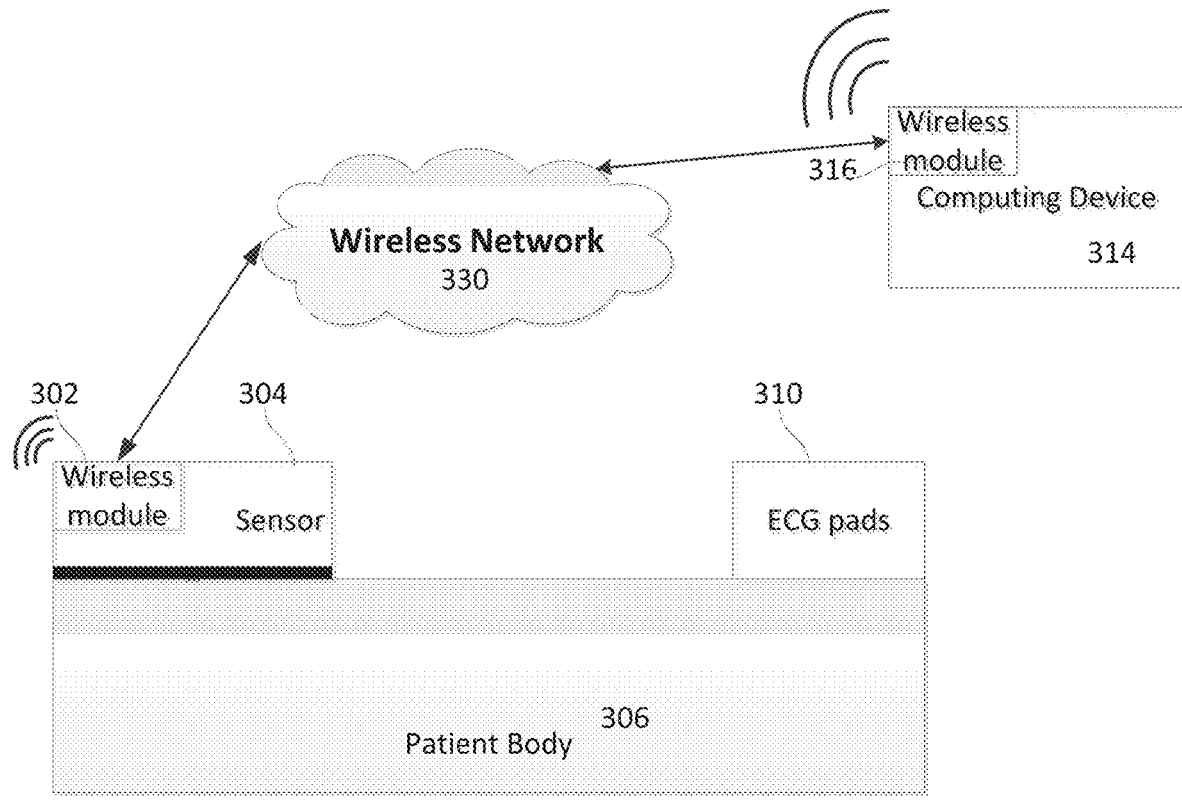

FIGS. 3A and 3B show signal paths used to establish and provide a signal transmission path between a sensor and a computing device. After initialization, the sensor 304 communicates with the computing device 314 wirelessly (FIG. 3B). As described above, is important to ensure that the sensor 304 is associated with the correct patient (and thereby associated with the correct computing device 314). In some examples, network membership can be based at least in part on signals that are sent across the body of the patient 306 (e.g., FIG. 3A). Sending signals across the body of the patient 306, e.g., using the patient's body as the conductor, ensures that the sensor is in contact with the same patient as the pads of the defibrillator, thereby confirming that they sensor is connecting to the correct patient-specific network.

More particularly, a sensor 304 is in contact with the surface of a patient's body 306 and ECG pads 310 are also in contact with the surface of the patient's body 306. The ECG pads 310 are connected via a wired connection 312 to the computing device 314 such as a defibrillator, which provides a wireless network. Thus, sending an authentication signal across the patient's body 306 along signal path 308 establishes that the sensor 304 is associated with the same patient as the ECG pads 310 which are connected to computing device 314.

The authentication signal can be any signal used during the process of confirming that the sensor should be granted access to the wireless network 330 established for the patient. It is not necessary that all signals used during authentication process be sent via the patient's body. Rather, sending/receiving at least one signal over the patient's body is sufficient to confirm that the sensor is in contact with the patient and should be allowed to access the patient-specific network. Once the authentication signal has been sent using the body as the conductor, then other signals can be sent wirelessly via a wireless network 330 using transmitters/receivers in wireless modules 302 and 316 of sensor 304 and computing device 314, respectively (FIG. 3B).

Figure 4:
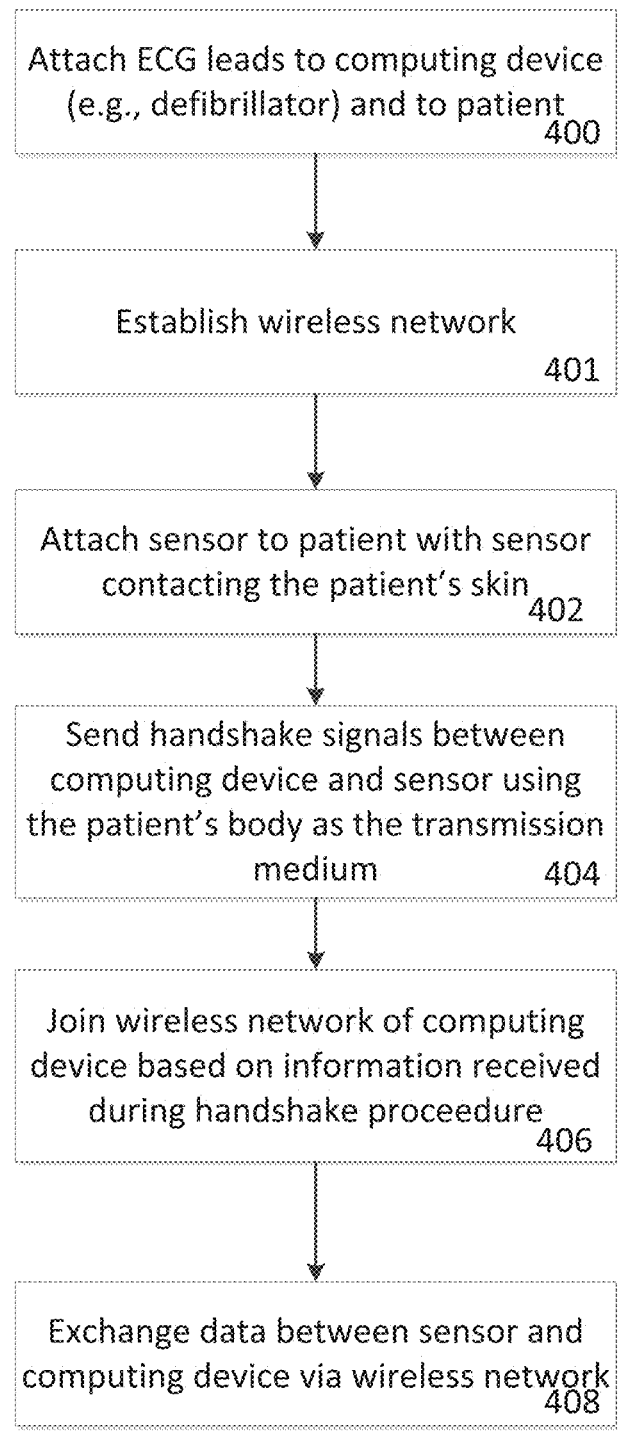
FIG. 4 is a flow chart of a process to join a patient-specific network.

FIG. 4 shows an exemplary process for establishing a wireless network associated with a patient and enabling sensors or other devices capable of wireless communication to join the wireless network for the patient. The process includes securing ECG leads to a patient and connecting the leads to a computing device such as a computing device included in a defibrillator (400).

Subsequent to attaching the ECG leads, a wireless network is established to provide a local or body area network in the vicinity of the patient (401). The network can take the form of an ad hoc, self-configuring, self-healing network such as a MESH network.

Sensors or other monitoring devices associated with the patient are subsequently deployed (402). These sensors and monitoring devices are configured to communicate using a wireless protocol with the computing device. However, prior to communicating wirelessly with the computing device the sensors and monitoring devices must join the established wireless network associated with the patient.

The sensors and other monitoring devices can join the wireless network by completing an authentication process such as a handshake process. In general, handshaking is an automated process of negotiation that dynamically sets parameters of a communications channel established between two entities before normal communication over the channel begins. It follows the physical establishment of the channel and precedes normal information transfer. Handshaking makes it possible to connect relatively heterogeneous systems or equipment over a communication channel without the need for human intervention to set parameters. While such handshaking could occur via the wireless communication channel, and the methods described herein, at least a portion of the handshaking signals are sent using the patient's body as the transmission medium (404). Sending at least one of the handshaking signals using the patient's body has the transmission medium confirms that the sensor is joining the correct wireless network, i.e. the wireless network associated with the patient that the sensor is monitoring.

The sensor or other monitoring device joins the wireless network based at least in part on the information received during the handshaking procedure (406). After joining the wireless network, additional exchange of data between the sensor or monitoring device and the computing device occurs via the wireless network (408).

Figure 5:
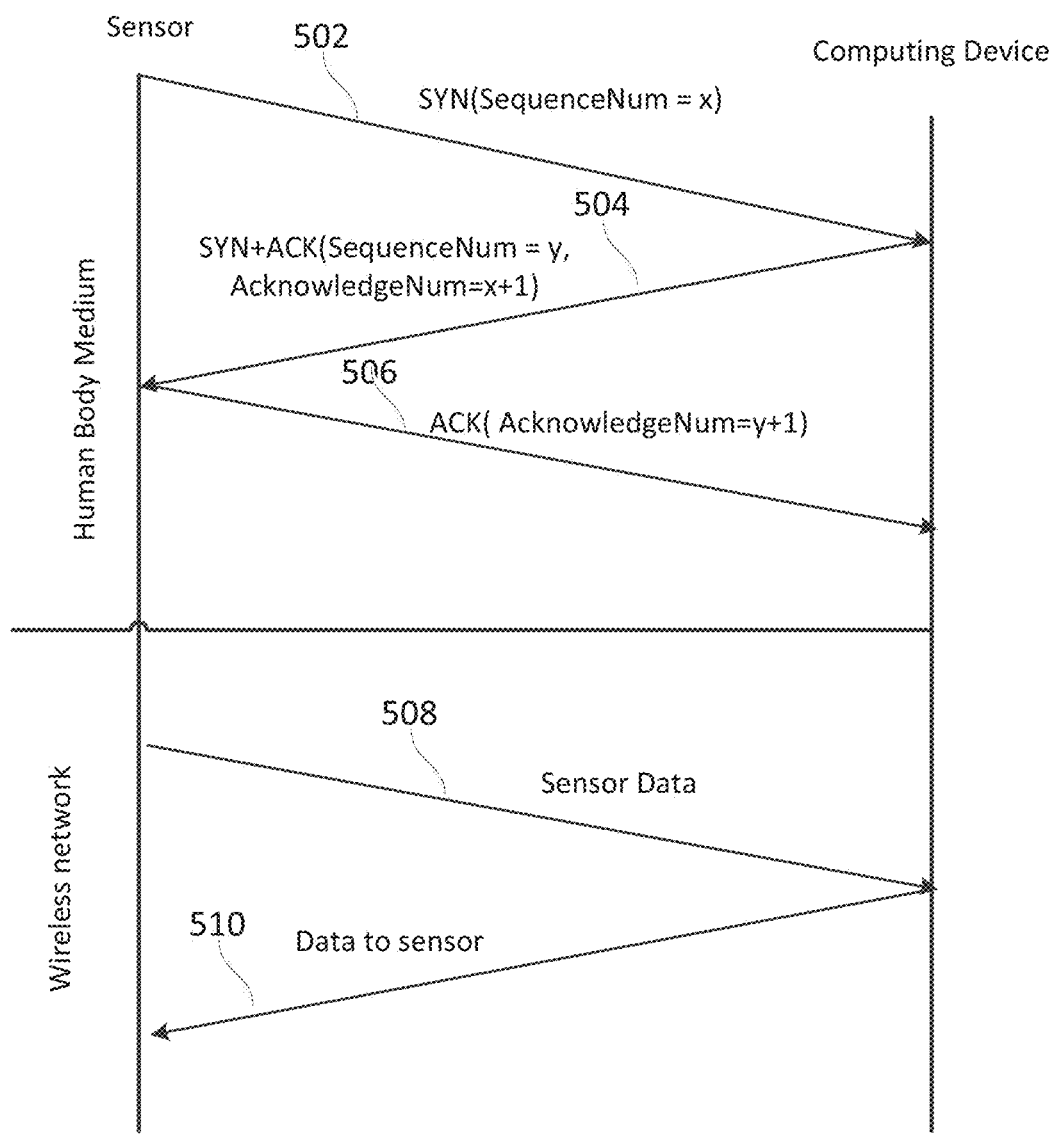
FIGS. 5 and 6 show exemplary authentication processes.

FIG. 5 shows an exemplary signaling process used to authenticate a sensor for a particular wireless network and to send and receive data between the sensor and the computing device. The exemplary signaling process utilizes a three-way handshake to perform the authentication. At least a portion of the three-way handshake occurs using the human body as the transmission medium to authenticate the sensor. After authentication, data is sent between the sensor and the computing device via a wireless network.

More particularly, in order to establish the connection, the sensor sends the computing device a "synchronize" (SYN) message 502 with its own sequence number. The computing device receives the synchronize message using the body transmission medium. Thus, the computing device will only receive the synchronize message if the sensor is in physical contact with the patient.

Next, the computing device which provides the wireless network replies with a synchronize-acknowledgment (SYN-ACK) message 504 with its own sequence number and acknowledgement number which the sensor receives. In the example shown in FIG. 5, this signal is also sent using the body as a transmission medium. In other examples, since at least one signal has already been received using the body as a transmission medium, the synchronize-acknowledgment signal can be sent over the wireless transmission medium.

Upon receiving the synchronize-acknowledgment signal, the sensor replies with an acknowledgment message with acknowledgement number (506). The computing device receives acknowledgment message with the acknowledgement number (to which the computing device doesn't need to reply). The acknowledgment message with the acknowledgement number is sent using the body as a transmission medium. In other examples, since at least one signal has already been received using the body as a transmission medium. The acknowledgement number can be sent over the wireless transmission medium.

After the handshaking procedure has been completed, further signals are sent and received between the sensor and the computing device via the wireless network (e.g., signals 508, 510). Thus, the data collected by the sensor during a rescue attempt is sent via the wireless network. Additionally, data sent to the sensor during the rescue attempt is sent via the wireless network.

In the example described above, the signals for the handshake are each sent using the body as a transmission medium. However, it is not necessary for all of the signals during a handshake procedure to be sent using the body as the transmission medium. Rather, it is only necessary for one of the signals in the handshake process to be sent using the body as a transmission medium in order to establish that the sensor is connected to the same patient as the patient for which the wireless network is associated. For example, the sensor could always send signals via the wireless transmission medium (which may require a lower voltage for transmission) and the acknowledgment signal from the computing device could be sent via the body.

Figure 6:
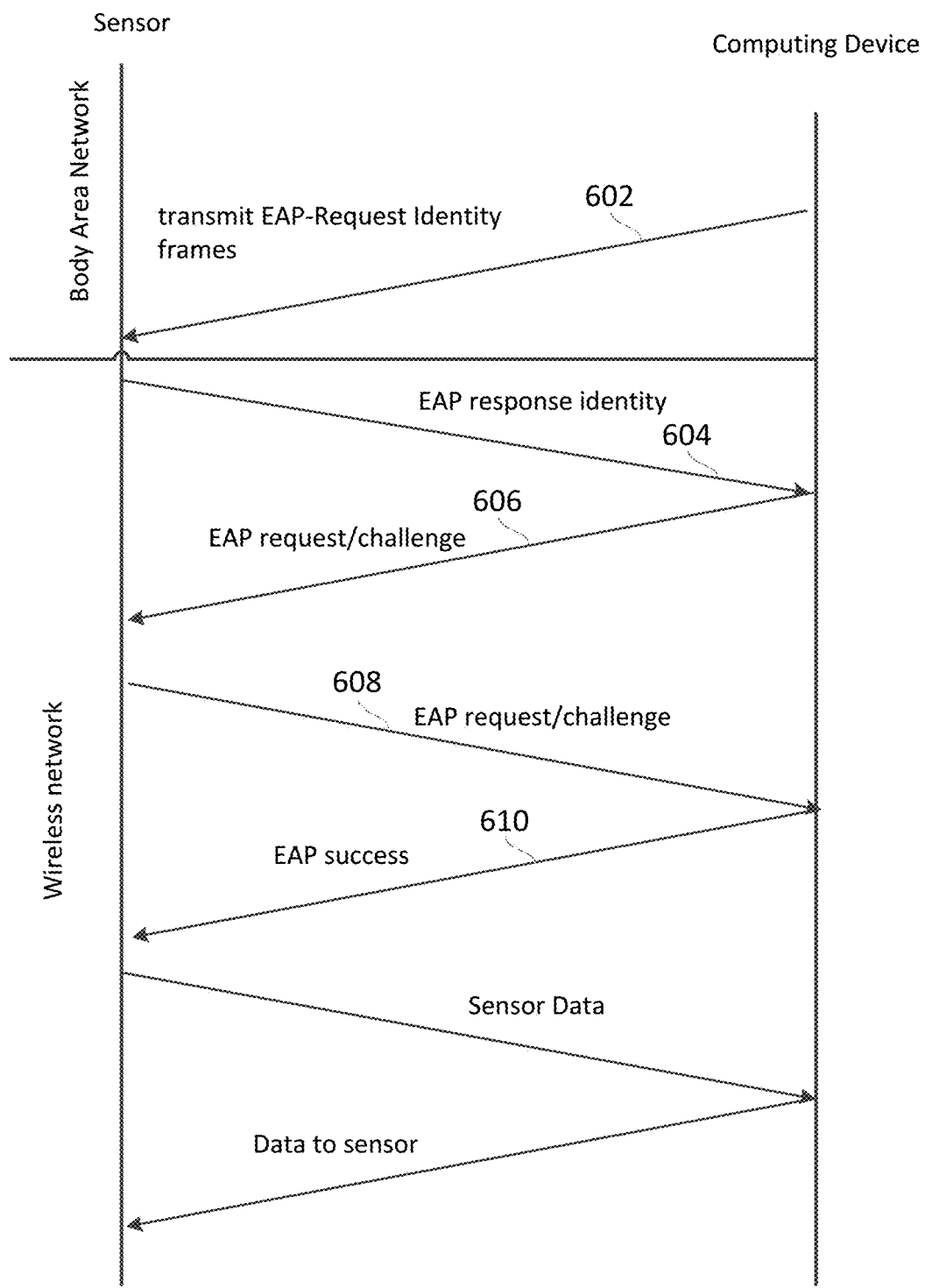

FIG. 6 shows another exemplary signaling process used to authenticate a sensor for a particular wireless network and to send and receive data between the sensor and the computing device. The authentication relies on at the Extensible Authentication Protocol, or EAP, which is an authentication framework frequently used in wireless networks and Point-to-Point connections. Examples of EAP protocols include the IEEE 802.11 (WiFi) the WPA and WPA2 standards which have adopted IEEE 802.1X with five EAP types as the official authentication mechanisms. In the methods described herein, at least one of the signals transmitted during the EAP authentication process used to access a network associated with a particular patient is transmitted using the patient's body as the conductive medium over which the signal travels to confirm that the sensor should be associated with the patient.

To initiate authentication the computing device periodically transmits EAP-Request Identity frames to a special Layer 2 address on the local network segment using the patient's body as the transmission medium (602). The sensor which has been placed in contact with the patient's skin listens on this address, and on receipt of the EAP-Request Identity frame (602) it responds with an EAP-Response Identity frame containing an identifier for the supplicant such as a User ID (604). This signal can be sent via the wireless network. A negotiation then begins (e.g., an EAP negotiation), EAP Requests and Responses are sent between the computing device and the sensor (606, 608) until the computing device responds with either an EAP-Success message (610), or an EAP-Failure message (not shown). If authentication is successful, the computing device allows access for the sensor to the wireless network (e.g., a port to the "authorized" state and normal traffic is allowed).

A number of embodiments have been described. Nevertheless, it will be understood that various modifications can be made without departing from the spirit and scope of the processes and techniques described herein. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A medical device system for providing a localized, patient-specific wireless network, the system comprising:
   an external defibrillator configured to provide a wireless network according to a wireless transmission protocol, wherein the external defibrillator includes a first wireless module that comprises a first transmitter and a first receiver configured to communicate via the wireless network;
   at least one sensor configured to be placed in contact with a skin of a patient and obtain patient-specific data, wherein the at least one sensor includes a second wireless module that comprises a second transmitter and a second receiver configured to communicate with the external defibrillator via the wireless network; and
   at least one defibrillator pad configured to be placed in contact with the skin of the patient, and configured to communicate with the external defibrillator over a wired electrical connection,
   wherein the external defibrillator is configured to communicate with the at least one sensor via a first signal transmission path and a second signal transmission path, the first signal transmission path comprising the wired electrical connection between the external defibrillator and the at least one defibrillator pad, and the second signal transmission path comprising a body of the patient as a conductive medium between the at least one defibrillator pad and the at least one sensor, and the external defibrillator is further configured to:
      establish the localized, patient-specific wireless network, wherein the localized, patient-specific wireless network includes the at least one sensor and the external defibrillator,
      perform a secure authentication process comprising an exchange of multiple authentication signals between the at least one sensor and the external defibrillator, the multiple authentication signals comprising:
         an initial signal transmitted from the second wireless module of the at least one sensor to the first wireless module of the external defibrillator via the wireless network according to the wireless transmission protocol, wherein the initial signal establishes communication between the at least one sensor and the external defibrillator, and
         an electrical reply signal from the external defibrillator to the at least one sensor, in response to the initial signal, transmitted over the first signal transmission path and the second signal transmission path; and
      subsequent to the secure authentication process, enable the at least one sensor to send and receive signals via the localized, patient-specific wireless network; and
   wherein the secure authentication process ensures that the at least one sensor is correctly paired with the external defibrillator and the localized, patient-specific wireless network associated with the patient so that the patient-specific data is only received by recipients authorized to view and use the patient-specific data.

2. The system of claim 1, wherein the external defibrillator is configured to initiate the secure authentication process based on a request to join the localized, patient-specific wireless network received from the at least one sensor.

3. The system of claim 1, wherein the secure authentication process comprises a handshaking routine.

4. The system of claim 1, wherein the localized, patient-specific wireless network comprises a body area network.

5. The system of claim 1, wherein the localized, patient-specific wireless network comprises a mesh network.

6. The system of claim 1, wherein the at least one sensor is configured to monitor at least one of blood pressure, temperature, respiration rate, blood oxygen level, end tidal carbon dioxide level, pulmonary function, and blood glucose level.

7. The system of claim 6 wherein the external defibrillator is configured to receive, from the at least one sensor via the localized, patient-specific wireless network, one or more wireless signals indicative of at least one of blood pressure, temperature, respiration rate, blood oxygen level, end tidal carbon dioxide level, pulmonary function, and blood glucose level.

8. The system of claim 1, wherein the multiple authentication signals comprise an identification signal that originates at the at least one sensor, and includes an identifier associated with the at least one sensor.

9. The system of claim 8, wherein the multiple authentication signals comprise an acknowledgement signal that originates at the external defibrillator, and includes an identifier uniquely identifying the acknowledgement signal.

10. The system of claim 1, wherein the secure authentication process comprises transmitting, by the external defibrillator, an identification request signal.

11. The system of claim 10, wherein the secure authentication process comprises transmitting, by the at least one sensor and in response to receiving the identification request signal, an identifier associated with the at least one sensor.

12. The system of claim 1, wherein the secure authentication process comprises using an authentication protocol.

13. The system of claim 12, wherein the authentication protocol is an Extensible Authentication Protocol (EAP).

14. The system of claim 1, wherein the multiple authentication signals are transmitted in accordance with a protected access protocol.

15. The system of claim 1, wherein the initial signal includes an authentication signal, and the electrical reply signal comprises an acknowledgement of the authentication signal, wherein the electrical reply signal is transmitted before the at least one sensor is enabled to send or receive signals via the localized, patient-specific wireless network.

16. The system of claim 1, wherein the initial signal is transmitted from the at least one sensor to the external defibrillator, and comprises a synchronize message that includes a first sequence number.

17. The system of claim 16, wherein the electrical reply signal is transmitted from the external defibrillator to the at least one sensor, and comprises a synchronize-acknowledgement message that includes a second sequence number and a first acknowledgement number.

18. The system of claim 17, wherein the initial signal is a first signal, the electrical reply signal is a second signal, and the multiple authentication signals comprises a third signal transmitted from the at least one sensor to the external defibrillator over the wired electrical connection and via the body of the patient.

19. The system of claim 18, wherein the third signal comprises an acknowledgement message that includes a second acknowledgement number.

20. The system of claim 1 wherein the at least one sensor is configured to always transmit signals via the wireless network and is configured to receive signals via the wireless network, and via the wired electrical connection and the body of the patient.

21. The system of claim 1, wherein the wireless transmission protocol includes a transmission protocol according to IEEE 802.11.

22. A method for providing a patient-specific wireless network, the method comprising:
 establishing, by an external defibrillator, the patient-specific wireless network, wherein the patient-specific wireless network comprises the external defibrillator configured to provide a wireless network according to a wireless transmission protocol, and wherein the external defibrillator includes a first wireless module that comprises a first transmitter and a first receiver configured to communicate via the wireless network;
 configuring at least one sensor to be placed in contact with a skin of a patient, wherein the at least one sensor includes a second wireless module that comprises a second transmitter and a second receiver configured to communicate with the external defibrillator via the wireless network,
 wherein the sensor is further configured to communicate with the external defibrillator via a first signal transmission path and a second signal transmission path, the second signal transmission path comprising a body of the patient as a conductive medium between the at least one sensor and at least one defibrillator pad in contact with the patient's skin, and the first signal transmission path comprising a wired electrical connection between the external defibrillator and the at least one defibrillator pad;
 performing a secure authentication process comprising exchanging multiple authentication signals between the at least one sensor and the external defibrillator, the multiple authentication signals comprising:
  an initial signal transmitted from the second wireless module of the at least one sensor to the first wireless module of the external defibrillator via the wireless network according to the wireless transmission protocol, wherein the initial signal establishes communication between the at least one sensor and the external defibrillator, and
  an electrical reply signal, in response to the initial signal, from the external defibrillator to the at least one sensor, transmitted over the first signal transmission path and the second signal transmission path; and
  subsequent to the authentication of the at least one sensor, enabling the at least one sensor to send and receive signals via the patient-specific wireless network; and
 wherein the secure authentication process ensures that the at least one sensor is correctly paired with the external defibrillator and the localized, patient-specific wireless network associated with the patient so that patient-specific data is only received by recipients authorized to view and use the patient-specific data.

23. The method of claim 22, wherein performing the secure authentication process comprises performing a handshaking routine.

24. The method of claim 22, wherein the patient-specific wireless network comprises a body area network.

25. The method of claim 22, wherein the patient-specific wireless network comprises a mesh network.

26. The method of claim 22, further comprising:
 securing the at least one defibrillator pad to the body of the patient; and
 securing the at least one sensor to the body of the patient.

27. The method of claim 22 comprising receiving, by the first wireless module of the external defibrillator, from the second wireless module of the at least one sensor via the patient-specific wireless network, one or more wireless signals indicative of at least one of blood pressure, temperature, respiration rate, blood oxygen level, end tidal carbon dioxide level, pulmonary function, and blood glucose level.

28. The method of claim 22, wherein the wireless transmission protocol includes a transmission protocol according to IEEE 802.11.

* * * * *